United States Patent
Nakano

(10) Patent No.: US 9,821,120 B2
(45) Date of Patent: Nov. 21, 2017

(54) PREFILLED SYRINGE, GASKET FOR USE IN PREFILLED SYRINGE, AND GASKET PRODUCTION METHOD

(71) Applicant: SUMITOMO RUBBER INDUSTRIES, LTD., Kobe-shi, Hyogo (JP)

(72) Inventor: Hiroaki Nakano, Kobe (JP)

(73) Assignee: SUMITOMO RUBBER INDUSTRIES, LTD., Kobe-shi, Hyogo (JP)

( * ) Notice: Subject to any disclaimer, the term of this patent is extended or adjusted under 35 U.S.C. 154(b) by 90 days.

(21) Appl. No.: 15/000,898

(22) Filed: Jan. 19, 2016

(65) Prior Publication Data

US 2016/0235919 A1  Aug. 18, 2016

(30) Foreign Application Priority Data

Feb. 18, 2015 (JP) ................. 2015-029794

(51) Int. Cl.

| | |
|---|---|
| A61M 5/315 | (2006.01) |
| F16J 9/20 | (2006.01) |
| F16J 9/28 | (2006.01) |
| B29C 63/00 | (2006.01) |
| B29L 31/26 | (2006.01) |

(52) U.S. Cl.
CPC ........ A61M 5/31513 (2013.01); A61M 5/315 (2013.01); A61M 5/31511 (2013.01);
(Continued)

(58) Field of Classification Search
CPC .......... A61M 5/31513; A61M 5/31515; A61M 5/315; A61M 5/31511; A61M 2207/00;
(Continued)

(56) References Cited

U.S. PATENT DOCUMENTS

| | | | | |
|---|---|---|---|---|
| 4,997,423 A | * | 3/1991 | Okuda ................ | A61M 5/2429 604/218 |
| 6,090,081 A | | 7/2000 | Sudo et al. | |

(Continued)

FOREIGN PATENT DOCUMENTS

| | | |
|---|---|---|
| EP | 2565006 A2 | 3/2013 |
| EP | 2703024 A1 | 3/2014 |

(Continued)

*Primary Examiner* — Manuel Mendez
(74) *Attorney, Agent, or Firm* — Birch, Stewart, Kolasch & Birch, LLP

(57) ABSTRACT

When a laminated gasket product is demolded from a mold in production thereof by a conventional production process, the gasket product is rubbed against the mold and, therefore, minute scratches are formed on a surface of the gasket product. The minute scratches may impair the reliable sealability of a liquid drug. A method for producing a gasket (13) for use in a prefilled syringe (10) includes the steps of: preparing a gasket forming mold; molding a gasket (13) in the mold, the gasket having a surface laminated with a lamination film (15) and including a circumferential surface portion (17); demolding the gasket (13) from the mold, and then simultaneously forming a groove (22) and a projection (24) each extending circumferentially of the gasket in a portion of the lamination film (15) present in the circumferential surface portion (17) of the gasket.

9 Claims, 2 Drawing Sheets

(52) U.S. Cl.
CPC ...... *B29C 63/0004* (2013.01); *B29C 63/0073* (2013.01); *F16J 9/20* (2013.01); *F16J 9/28* (2013.01); *A61M 2207/00* (2013.01); *B29L 2031/265* (2013.01)

(58) Field of Classification Search
CPC ...... B29C 63/004; B29C 63/0073; F16J 9/20; F16J 9/28; B29L 2031/265
USPC .............................. 604/222, 228–230, 218
See application file for complete search history.

(56) References Cited

U.S. PATENT DOCUMENTS

| | | | | |
|---|---|---|---|---|
| 6,315,758 | B1 * | 11/2001 | Neer | A61M 5/14546 604/152 |
| 7,766,882 | B2 * | 8/2010 | Sudo | A61M 5/31511 604/218 |
| 2006/0178643 | A1 | 8/2006 | Sudo et al. | |
| 2013/0040156 | A1 | 2/2013 | Nakano et al. | |
| 2014/0339777 | A1 | 11/2014 | Nakano et al. | |

FOREIGN PATENT DOCUMENTS

| | | |
|---|---|---|
| EP | 2703025 A1 | 3/2014 |
| JP | 7-25953 Y2 | 6/1995 |
| JP | 3282322 B2 | 5/2002 |
| JP | 3387775 B2 | 3/2003 |
| JP | 2003-190285 A | 7/2003 |
| JP | 2006-181027 A | 7/2006 |
| JP | 4908617 B2 | 4/2012 |
| JP | 2014-46096 A | 3/2014 |
| JP | 2014-223149 A | 12/2014 |
| JP | 2015-146871 A | 8/2015 |

* cited by examiner

PREFILLED SYRINGE, GASKET FOR USE IN PREFILLED SYRINGE, AND GASKET PRODUCTION METHOD

TECHNICAL FIELD

The present invention relates to a prefilled syringe, particularly, to a gasket for use in the prefilled syringe and a gasket production method.

BACKGROUND ART

Syringes prefilled with a liquid drug (prefilled syringes) are used as medical syringes. In recent years, the prefilled syringes are increasingly used, because the prefilled syringes can be easily handled without the need for transferring a liquid drug into the syringe and can prevent medical malpractice such as transfer of a wrong liquid drug into the syringe.

Unlike conventional syringes (into which a liquid drug sucked up from a vial or other container is transferred immediately before use), the prefilled syringes are required to serve as a container which is kept in contact with the liquid drug for a long period of time.

A gasket to be used for such a syringe is generally made of a crosslinked rubber. It is known that the crosslinked rubber typically contains various crosslinking components, and these crosslinking components and their thermally decomposed products are liable to migrate into the liquid drug when the liquid drug is kept in contact with the gasket. It is also known that these migrating components adversely influence the efficacy and the stability of some liquid drug.

When the prefilled syringe is used, the gasket is required to smoothly slide with respect to a syringe barrel of the syringe. In general, the gasket made of the crosslinked rubber cannot be used because of its poorer slidability. Therefore, it is a general practice to apply a silicone oil onto a surface of the barrel or the gasket. However, it is known that the silicone oil adversely influences the efficacy and the stability of some liquid drug.

From this viewpoint, a so-called laminated gasket product is known, which includes a rubber gasket body having a surface laminated with a highly slidable film. By covering the surface of the rubber gasket body with the film, the components of the crosslinked rubber are prevented from migrating into the liquid drug. Further, sufficient slidability is ensured by laminating the surface with the highly slidable film.

Exemplary materials for the film to be used for these purposes include ultrahigh molecular weight polyethylenes and fluororesins which are highly slidable. Of these materials, the fluororesins are preferred because of their high slidability and chemical stability. Of these fluororesins, polytetrafluoroethylenes (PTFE) are particularly preferred because of their very high slidability and stability.

CITATION LIST

Patent Document

Patent Document 1: Japanese examined utility model application publication No. HEI 7(1995)-25953

SUMMARY OF THE INVENTION

Problem to be Solved by the Invention

However, the film to be used for the aforementioned purposes does not have rubber elasticity and, therefore, impairs the rubber elasticity of the inside crosslinked rubber. The rubber elasticity of the gasket is essential for reliable sealing of the liquid drug contained in the syringe barrel. If the gasket has insufficient rubber elasticity, leakage of the inside liquid drug will result.

To cope with this problem, the inventors of the present invention further conducted studies to control the thickness of the film to be employed for the lamination and modify the surface of the film for improvement of the film.

In a general rubber product production process, a rubber is vulcanization-molded into a desired product shape in a mold having a cavity conformal to the desired product shape, and then the resulting product is demolded from the mold. In this production process, the product is rubbed against the mold when being demolded from the mold and, therefore, minute scratches are formed on the surface of the product. In a gasket production process, the gasket product is taken out of the mold in a direction perpendicular to the circumference of the product. Scratches formed in the perpendicular direction on the surface of the gasket are unwanted, because the reliable sealability of the liquid drug is significantly impaired by the scratches.

In the molding of the laminated gasket, the surface of the gasket body is laminated with a less fluid film layer, so that the cavity of the mold is not perfectly filled. Therefore, the product has insufficient shape followability with respect to the cavity of the mold. Even if a minute groove structure is formed in an inner surface of the cavity of the mold, it is difficult to produce a molded product with the groove structure perfectly transferred to the film layer on the surface of the gasket body.

Solution to Problem

The inventors of the present invention made an attempt to alleviate these problems by forming a minute groove structure in a circumferential surface of the gasket after the gasket laminated with the film is produced.

With the minute groove structure formed circumferentially in the surface of the gasket, more specifically, a compressive stress is increased in a portion of the gasket around a groove within the syringe barrel to ensure the reliable sealing. Further, the scratches formed in the direction perpendicular to the circumference of the gasket when the gasket is taken out of the mold can be filled by forming the minute groove structure circumferentially of the gasket after the molding of the gasket.

As a result of intensive studies, the inventors of the present invention found that the compressive stress can be further increased by simultaneously forming a projection and the groove, and attained the present invention.

According to inventive aspects defined by claims 1 to 5, there is provided a gasket for use in a prefilled syringe. According to inventive aspects defined by claims 6 and 7, there is provided a prefilled syringe. According to inventive aspects defined by claims 8 to 10, there is provided a gasket production method.

According to the inventive aspect of claim 1, more specifically, the gasket for use in the prefilled syringe includes a main body made of an elastic material and a lamination film provided on a surface of the main body, and the gasket has a circumferential surface portion to be kept in contact with an inner peripheral surface of a syringe barrel of the syringe, wherein the lamination film has a groove and a projection provided in a surface portion thereof present in the circumferential surface portion of the gasket as each extending circumferentially of the gasket.

According to the inventive aspect of claim 2, a portion of the lamination film formed with the groove has a thickness that is smaller by 1 μm to 50 μm than a thickness of a portion of the lamination film not formed with the groove, and a portion of the lamination film formed with the projection has a thickness that is greater by 1 μm to 10 μm than a portion of the film not formed with the projection in the gasket of claim 1.

According to the inventive aspect of claim 3, the groove includes a plurality of grooves, and the projection includes a plurality of projections in the gasket of claim 1 or 2.

According to the inventive aspect of claim 4, the groove includes at least one annular groove extending circumferentially around the circumferential surface portion, and the projection includes at least one projection extending circumferentially around the circumferential surface portion in the gasket of claim 1 or 2.

According to the inventive aspect of claim 5, the lamination film has a thickness of not less than 20 μm and not greater than 50 μm in the gasket of any one of claims 1 to 4.

According to the inventive aspect of claim 6, the prefilled syringe includes a tubular syringe barrel, a plunger combined with the syringe barrel and reciprocally movable in the syringe barrel, and a gasket attached to a distal end of the plunger, the gasket being the gasket of any one of claims 1 to 5.

According to the inventive aspect of claim 7, the projection of the gasket contacts the syringe barrel at a contact pressure of not less than 5 MPa in the prefilled syringe of claim 6.

According to the inventive aspect of claim 8, the gasket production method for producing the gasket for use in the prefilled syringe includes the steps of: preparing a gasket forming mold; molding a gasket in the mold, the gasket having a surface laminated with a lamination film and including a circumferential surface portion; demolding the gasket from the mold, and then simultaneously forming a groove and a projection each extending circumferentially of the gasket in a portion of the lamination film present in the circumferential surface portion of the gasket.

According to the inventive aspect of claim 9, a laser processing process is employed in the simultaneous groove/projection forming step in the gasket production method of claim 8.

According to the inventive aspect of claim 10, two or more grooves and two or more projections are formed in the simultaneous groove/projection forming step in the gasket production method of claim 8 or 9.

Effects of the Invention

According to the present invention, the laminated gasket for the prefilled syringe has excellent sealability.

According to the present invention, the prefilled syringe is excellent in sealability and does not adversely influence the efficacy and the stability of the liquid drug even if being kept in contact with the liquid drug for a long period of time.

According to the present invention, the production method can produce the laminated gasket having excellent sealability.

EMBODIMENTS OF THE INVENTION

With reference to the attached drawings, one embodiment of the present invention will hereinafter be described specifically.

Figure 1:
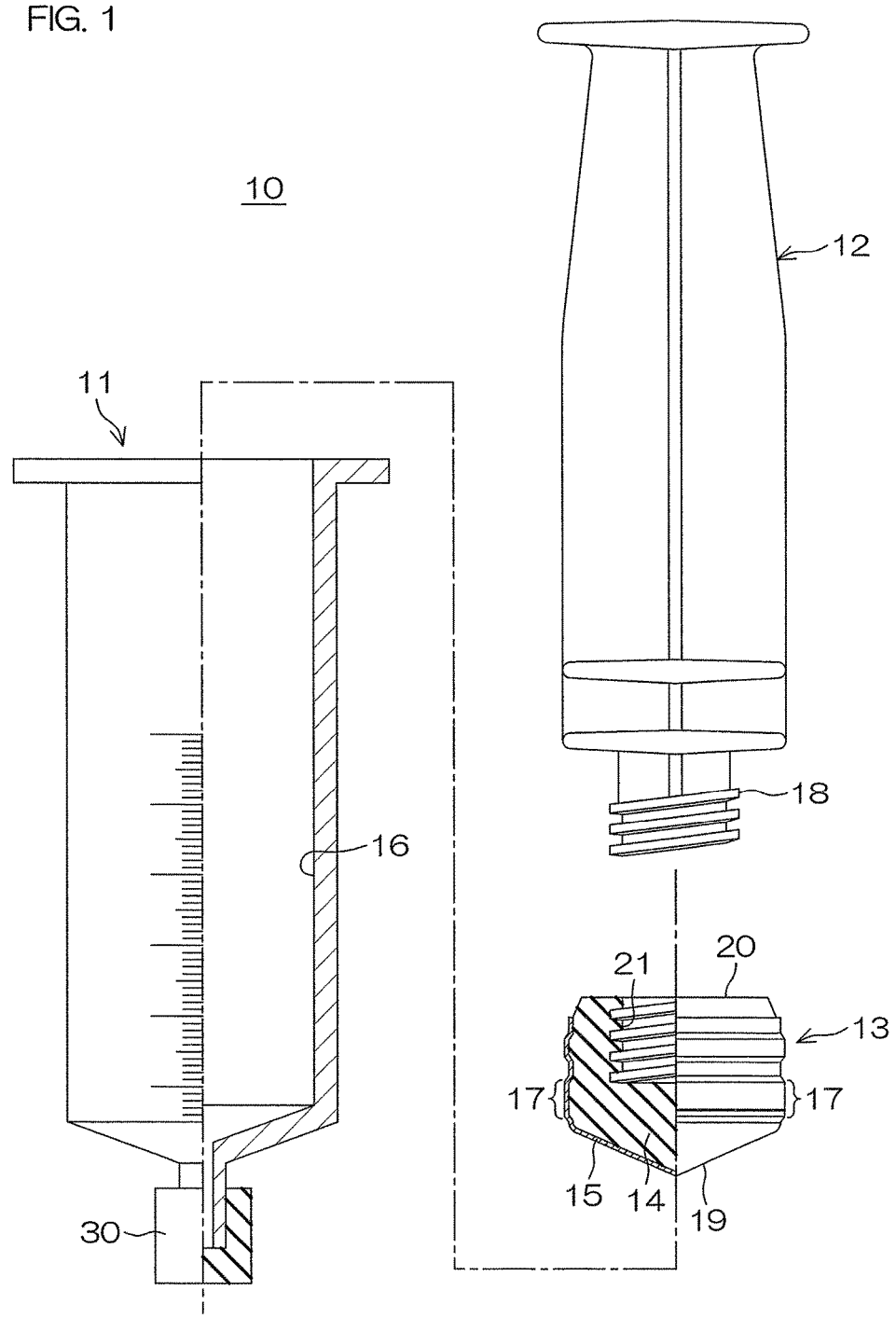
FIG. 1 is a diagram illustrating a prefilled syringe according to one embodiment of the present invention in an exploded state.

FIG. 1 is a diagram illustrating a prefilled syringe according to one embodiment of the present invention in an exploded state. In FIG. 1, a syringe barrel 11, a distal end cap 30 and a gasket 13 are shown half in section.

Referring to FIG. 1, the prefilled syringe 10 includes a hollow cylindrical syringe barrel 11, and a plunger 12 combined with the syringe barrel 11 and reciprocally movable in the syringe barrel 11, and a gasket 13 attached to a distal end of the plunger 12. The gasket 13 is a laminated gasket which includes a main body 14 made of an elastic material (a rubber, an elastomer or the like), and a lamination film 15 provided on a surface of the main body 14. The gasket 13 has a circumferential surface portion 17 which is kept in gas-tight and liquid-tight contact with an inner peripheral surface 16 of the syringe barrel 11.

The plunger 12 includes a resin plate piece, for example, having a cross shape as seen in section, and a head 18 provided at a distal end of the resin plate piece and fitted with the gasket 13. The head 18 is an integral part of the plunger 12 made of a resin and shaped in a male screw.

The gasket 13 has a generally cylindrical shape having a short axis. The gasket 13 has a distal end face, for example, having a conical center portion projecting at an obtuse angle, and a rear end face axially recessed into an engagement recess 21 shaped in a female screw. The head 18 of the plunger 12 is screwed into the engagement recess 21 of the gasket 13, whereby the gasket 13 is attached to the distal end of the plunger 12.

Figure 2:
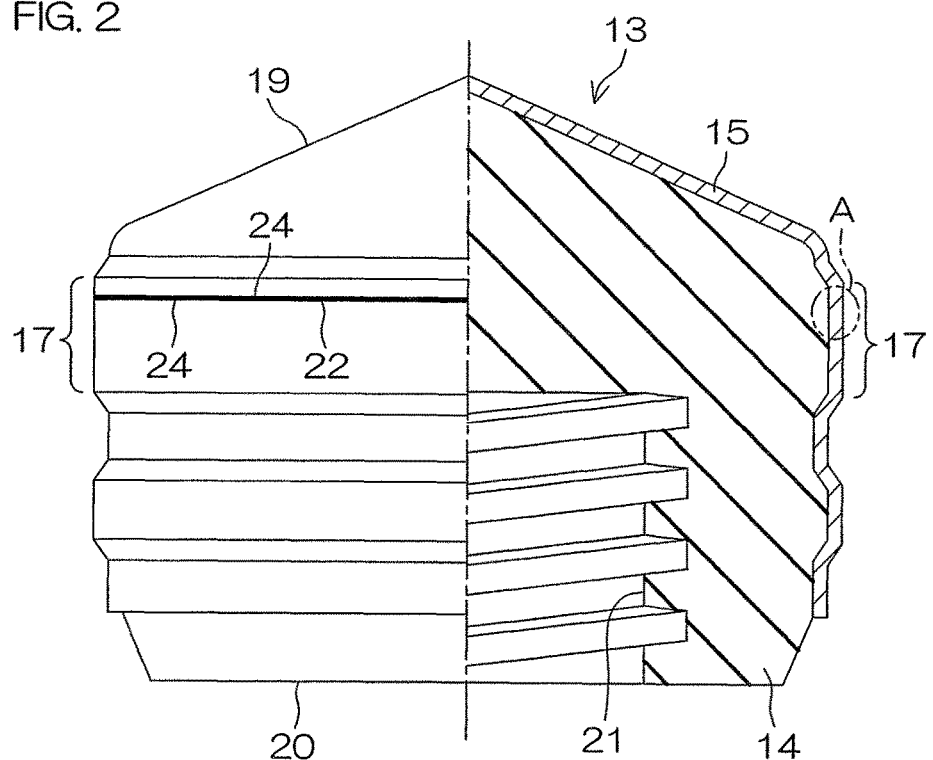
FIG. 2 is a diagram of a laminated gasket according to the embodiment of the present invention with a half of the gasket illustrated in section.

FIG. 2 is a diagram showing only the gasket 13 of FIG. 1 on an enlarged scale with a half of the gasket 13 shown in section. In FIG. 2, the gasket 13 is illustrated in a state inverted from the state shown in FIG. 1.

Referring to FIG. 2, the structure of the gasket 13 according to this embodiment will be described in greater detail.

The gasket 13 includes the main body 14, and the lamination film 15 provided on the surface of the main body 14. The main body 14 is merely required to be made of an elastic material, which is not particularly limited. Examples of the elastic material include thermosetting rubbers and thermoplastic elastomers. Particularly, the thermosetting rubbers and dynamically crosslinkable thermoplastic elastomers having crosslinking sites are more preferred because they are highly heat-resistant. The polymer component is not particularly limited, but preferred examples of the polymer component include ethylene-propylene-diene rubbers and butadiene rubbers which are excellent in moldability. Other preferred examples of the polymer component include butyl rubbers, chlorinated butyl rubbers and brominated butyl rubbers which are excellent in gas permeation resistant.

The type of the lamination film 15 to be provided on the surface of the main body 14 is not particularly limited, as long as the lamination film is capable of preventing migration of substances from the crosslinked rubber (main body 14) and has more excellent slidability, i.e., a smaller friction coefficient, than the rubber. Examples of the lamination film include films of very high molecular weight polyethylenes and fluororesins which are proved to be practical in medical applications. Particularly, the fluororesins are preferred because they are excellent in slidability and surface chemical stability. Usable examples of the fluororesins include conventionally known fluorine-containing resins, such as PTFE, modified PTFE, ethylene tetrafluoroethylene copolymers (ETFE) and perfluoroalkyl ether polymers (PFA). The PTFE and the modified PTFE are preferred because of their excellent slidability and chemical stability. The ETFE is preferred because of its resistance to γ-ray sterilization. For adhesiveness to the main body 14, a film made of a mixture of these resins or a laminate film of these resins may be used.

Features of the laminated gasket 13 according to this embodiment are that the gasket 13 includes the circumferential surface portion 17 to be kept in gas-tight and liquid-tight contact with the inner peripheral surface 16 of the syringe body 11, and that a groove 22 and projections 24 are formed in a surface portion of the lamination film 15 present in the circumferential surface portion 17 as extending circumferentially of the gasket 13.

Figure 3:
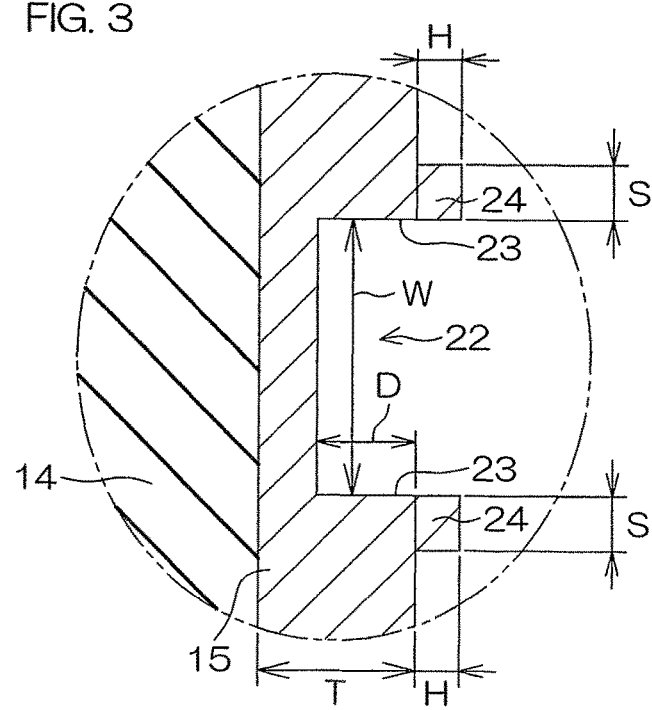
FIG. 3 is an enlarged sectional view of a portion A in FIG. 2.

FIG. 3 is an enlarged sectional view of a portion A in FIG. 2. Referring to FIGS. 2 and 3, the laminated gasket 13 will be described.

The circumferential direction in which the groove 22 and the projections 24 extend is as shown in FIG. 2. That is, the circumferential direction is perpendicular to the axial direction of the generally cylindrical gasket 13. The circumferential direction may be generally horizontal, and may extend at a given angle within an angular range of the circumferential surface portion (hereinafter referred to as "peak portion") 17. If the groove 22 and the projections 24 are formed as extending at an angle outside the angular range of the peak portion 17, the liquid drug is liable to leak through the groove 22 and the projections 24. The circumferential direction preferably extends at an angle within a range of −10 to +10 degrees with respect to a horizontal plane.

The circumferential groove 22 and the circumferential projections 24 preferably each extend along the entire circumference of the peak portion 17 in order to provide a uniform effect throughout the circumference of the peak portion 17. The circumferential groove 22 and the circumferential projections 24 preferably each have a starting point and an end point coinciding with each other. By way of example, a single groove 22 and two projections 24 are preferably provided along the entire circumference of the peak portion 17. The expanded shape of each of the groove 22 and the projections 24 on the surface of the gasket 13 is not particularly specified, but the groove 22 and the projections 24 preferably each has a generally linear shape for elimination of local directionality.

It is merely necessary to provide at least one groove 22 and at least one projection 24 with no upper limits in the number of the grooves 22 and the number of the projections 24.

If the groove 22 and the projections 24 each have a length smaller than the entire circumference of the peak portion 17, a plurality of grooves 22 and a plurality of projections 24 may be provided, at least one of which preferably extends along the entire circumference of the peak portion 17 to provide the uniform effect throughout the entire circumference.

The groove 22 and the projections 24 are formed after the formation of the gasket 13. If the formation of the groove 22 and the projections 24 is achieved simultaneously with the molding of the gasket 13, i.e., if a groove/projection structure corresponding to the groove 22 and the projections 24 is preliminarily formed in the mold and transferred to the lamination film, the groove 22 and the projections 24 thus formed would be scratched or damaged during the demolding. Where the groove 22 and the projections 24 are formed after the molding of the gasket, in contrast, the scratches formed during the molding and the demolding of the gasket can be repaired to some extent in the subsequent groove/projection forming step.

Conceivable methods for forming the groove 22 and the projections 24 include: a plastic deformation method in which the gasket 13 made of a laminate of the film 15 and the rubber 14 is plastically deformed by application of an external stress; and a cutting method in which the surface layer of the gasket 13, i.e., the lamination film 15, is cut to be formed with the groove 14 and the projections 24. Of these methods, the cutting method is more preferred, because the groove and the projections can be more easily formed by the cutting method than by the plastic deformation method and the stress is less liable to influence the other portion of the film 15 not formed with the groove and the projections.

The cutting may be achieved in a known manner by employing a cutting blade or irradiation with a laser beam not by way of limitation. The cutting by the irradiation with the laser beam is more preferred because the minute groove structure can be easily formed and the stress is less liable to influence a portion of the film around the groove/projection formation portion.

Where the cutting is achieved by the irradiation with the laser beam, the type and the output of the laser beam may be determined in conformity with a conventional technique. The type of the laser beam may be properly selected according to the type of the film to be used and the depth of the groove, and an infrared laser beam is preferred because of its industrially easy handling. The irradiation period may be properly selected according to the cutting conditions. Particularly, irradiation with a short-pulse laser beam is preferred with little thermal influence on the portion of the film around the groove/projection formation portion.

The groove 22 to be formed by the cutting preferably has a depth D of not less than 1 µm and not greater than 50 µm, preferably not less than 5 µm and not greater than 15 µm. In general, the film 15 to be employed for the laminated gasket 13 preferably has a smaller thickness T. If the thickness T is excessively small, however, the cutting is difficult. Therefore, the thickness T is practically about 20 µm to about 50 µm. Generally, it is not preferred that the underlying rubber layer 14 is exposed by the cutting of the film 15. Therefore, the upper limit of the depth D of the groove 22 is preferably not greater than the thickness of the film 15. The lower limit of the depth D is preferably 1 µm. A groove depth D of smaller than 1 µm is not preferred, because the groove 22 fails to provide the intended effects due to a problem associated with the processing accuracy. A groove depth D of not smaller than 5 µm is preferred for easy and uniform formation of the groove 22.

The width W of the groove 22 to be formed by the cutting may be properly selected according to the depth D of the groove and the physical properties of the film and the rubber, but is preferably not greater than 100 µm, more preferably not greater than 50 µm. An excessively great width W is not preferred because, when the gasket is inserted into the syringe barrel, a groove bottom is liable to be raised by the elasticity of the compressed rubber to be pressed against the inner surface of the syringe barrel with the groove structure changed. On the other hand, a groove width W of 1 µm or smaller is not preferred, because uniform cutting is impossible due to the processing accuracy to fail to provide the intended effects.

The sectional shape of the groove 22 to be formed is not particularly limited. For productivity, the groove preferably has a simply recessed sectional shape or a rounded recessed sectional shape.

A feature of the present invention is that the formation of the groove 22 and the formation of the projections 24 are simultaneously achieved. That is, the projections 24 are formed along side edges of the groove 22 by positively forming burrs in the formation of the groove 22.

Where the groove 22 is formed by the laser beam processing, a surface portion of the lamination film 15 is evaporated or decomposed by the laser beam, and a part of the material is re-deposited along the outer edges 23 of the groove 22 to form the projections 24.

The projections 24 to be formed preferably each have a height H of not smaller than 1 µm and not greater than 10 µm, more preferably not smaller than 3 µm and not greater than 7 µm. The projections 24 preferably each have a width S of not less than 3 µm and not greater than 50 µm, more preferably not less than 7 µm and not greater than 25 µm. In the present invention, only the projections 24 are kept in contact with the syringe barrel 11, thereby increasing a contact pressure between the gasket 13 and the syringe barrel 11. The projections 24 preferably each have a smaller size in order to increase the contact pressure. On the other hand, excessively minute processing more than necessary is not preferred for process efficiency.

In this embodiment, the projections 24 are respectively formed along the outer edges 23 of the groove 22. Alternatively, a single projection 24 may be formed along one of the outer edges 23 of the groove 22 by adjusting the irradiation direction of the laser beam.

Next, a method for producing the gasket 13 according to this embodiment will be described.

The gasket 13 according to this embodiment is produced through the following production process steps:
(1) Preparing a gasket molding mold;
(2) Molding a gasket having a surface laminated with a lamination film in the mold; and
(3) Demolding the laminated gasket from the mold, and then simultaneously forming a groove and projections in a surface of the lamination film circumferentially of a circumferential surface portion of the gasket.

In the step of molding the gasket having the surface laminated with the lamination film in the mold, an unvulcanized rubber is placed on an inner surface of the lamination film in the mold, and vulcanization-molded.

For example, a sheet of an unvulcanized rubber containing a crosslinking agent is stacked on a lamination film, and vulcanization-molded in the mold. Thus, a gasket having a predetermined shape is produced.

In this case, the inner surface of the lamination film 15 on which the rubber is placed is preferably preliminarily roughened. With the inner surface of the film 15 roughened, the rubber can firmly adhere to the film 15 by the vulcanization molding without the use of an adhesive agent. The adhesion is attributable to an anchoring effect which is created with the vulcanized rubber intruding into voids formed in the roughened inner surface of the film 15.

The modification (roughening) of the inner surface of the lamination film 15 may be achieved, for example, by applying ion beam to the inner surface to break the internal molecular structure in the inner surface (see, for example, JP4908617).

Another production method may be employed which includes the steps of applying an adhesive layer on an inner surface of a lamination film 15 not roughened, superposing an unvulcanized rubber material on the adhesive layer, and putting the lamination film and the rubber material in a mold to mold a gasket in the mold.

After the gasket is molded in the mold, the gasket is demolded from the mold, and the groove and the projections are simultaneously formed in a circumferential surface portion of the gasket. Thus, the gasket is produced as having excellent sealability.

The simultaneous formation of the groove and the projections is preferably achieved by the laser beam processing as described above.

EXAMPLES

Examples and Comparative Examples

Different types of lamination films were each used in combination with an unvulcanized rubber, and gaskets were produced by vulcanization molding of the rubber. Gasket products (Examples 1 to 8 and Comparative Examples 2 and 3) were each produced by forming a circumferential groove structure, and a gasket product (Comparative Example 1) was produced without forming a circumferential groove structure.

<Production Method>

Fluororesin PTFE film (VALFLON (registered trade name) available from Nippon Valqua Industries Ltd.)

Modified PTFE film (VALFLON Ex1 (registered trade name) available from Nippon Valqua Industries Ltd.)

ETFE film (Fluon ETFE (registered trade name) available from Asahi Glass Co., Ltd.)

The films were each treated for adhesion by the method disclosed in JP4908617. The thicknesses of the films are shown in Table 1.

Unvulcanized Rubber Sheet

Halogenated butyl rubber

Crosslinking Agent 2-di-n-butylamino-4,6-dimercapto-s-triazine Zisnet DB (registered trade name) available from Sankyo Kasei Co., Ltd.

Production Conditions

Vulcanization temperature: 180° C.

Vulcanization period: 8 minutes

Processing pressure: 20 MPa

Gasket products each had a product shape having a maximum diameter of 6.60 mm.

The formation of the groove was achieved by the following laser beam processing after the gaskets were molded as having the aforementioned product shape.

Laser Beam Processing

Apparatus: Multi-purpose manual laser processor available from Allied Lasers, Inc.

A hybrid laser was used as an oscillator to emit laser beam at a wavelength of 1064 nm. The laser beam had a processing spot diameter of 10 µm. A groove having a desired width was formed by repeatedly applying the laser beam. The shape of the groove and the shape of the projection were controlled by adjusting the output.

<Test Method>

Measurement of Dimensions of Groove and Projection

By means of a laser microscope (VK-X100 available from Keyence Corporation), the surface geometry of each of the products formed with the groove was measured with an objective lens having a magnification of 50×. For each of the products, the maximum depth and the width of the groove were measured at four positions on an image of the product, and arithmetic averages were determined for the maximum depth and the width. Further, the maximum depth and the width of the projection were measured in the same manner as described above on the image of the product. Where a distinct projection was not formed, "None" is given in Table 1.

Liquid Drug Sealability

The products thus obtained after the formation of the groove were each inserted in a syringe barrel, which was in turn filled with a test liquid. Then, an opposite end of the syringe barrel was capped. The resulting syringe barrel was allowed to stand still at 40° C. for one week, and observed with an objective lens having a magnification of 50× by means of a video microscope (DVM5000 available from Leica Microsystems Inc.) to be checked for liquid leakage. For each product, 20 samples were prepared, and the number of samples suffering from liquid leakage (in which the test liquid penetrated beyond a maximum diameter portion of the gasket) was recorded. A product with two or less samples suffering from the liquid leakage was rated as acceptable. The test liquid herein used was prepared by adding 0.2 g/liter of a colorant (Methylene Blue available from Sigma Aldrich Japan LLC.) and 1.0 g/liter of a surfactant (POLYSORBATE 80 available from NOF Corporation) to water. The syringe barrel was made of a cycloolefin resin and had an inner diameter of 6.35 mm.

This application corresponds to Japanese Patent Application No. 2015-029794 filed in the Japan Patent Office on Feb. 18, 2015, the disclosure of which is incorporated herein by reference in its entirety.

What is claimed is:

1. A gasket for use in a prefilled syringe comprising:
   a main body made of an elastic material; and
   a film laminated on a surface of the main body,
   wherein the gasket has a circumferential surface portion to be kept in contact with an inner peripheral surface of a syringe barrel of the syringe,
   wherein the film has a groove and a projection provided in a surface portion thereof present in the circumferential surface portion of the gasket as each extending circumferentially of the gasket,
   wherein a portion of the film formed with the groove has a thickness that is smaller by 1 μm to 50 μm than a thickness of a portion of the film not formed with the groove, and
   wherein a portion of the film formed with the projection has a thickness that is greater by 1 μm to 10 μm than a portion of the film not formed with the projection.

2. The gasket according to claim 1, wherein the groove includes a plurality of grooves, and the projection includes a plurality of projections.

3. The gasket according to claim 1, wherein the groove includes at least one annular groove extending circumferentially around the circumferential surface portion, and the

TABLE 1

|  | Example 1 | Example 2 | Example 3 | Example 4 | Example 5 | Example 6 | Example 7 | Example 8 |
|---|---|---|---|---|---|---|---|---|
| Type of film | PTFE | PTFE | PTFE | PTFE | PTFE | PTFE | Modified PTFE | ETFE |
| Processing method | Laser | Laser | Laser | Laser | Laser | Laser | Laser | Laser |
| Output (%) | 30 | 30 | 50 | 60 | 20 | 10 | 30 | 40 |
| Depth of grooves (μm) | 10.2 | 10.2 | 17.5 | 34.0 | 7.2 | 5.2 | 10.0 | 10.2 |
| Width of grooves (μm) | 15.7 | 15.4 | 20.8 | 40.3 | 15.2 | 10.3 | 15.2 | 12.5 |
| Number of grooves | 1 | 3 | 3 | 3 | 3 | 3 | 1 | 3 |
| Height of projections (μm) | 5.1 | 5.6 | 7.2 | 8.8 | 2.2 | 0.8 | 4.9 | 3.9 |
| Width of projections (μm) | 7.2 | 7.7 | 11.9 | 13.0 | 5.3 | 3 | 7.4 | 7.5 |
| Number of samples with liquid leakage | 0 | 0 | 0 | 1 | 1 | 2 | 0 | 1 |
| Evaluation | *1 | *1 | *1 | *1 | *1 | *1 | *1 | *1 |

|  | Comparative Example 1 | Comparative Example 2 | Comparative Example 3 |
|---|---|---|---|
| Type of film | PTFE | PTFE | ETFE |
| Processing method | — | Laser | Laser |
| Output (%) | — | 5 | 8 |
| Depth of grooves (μm) | — | 2.3 | 2.8 |
| Width of grooves (μm) | — | 5.5 | 6.6 |
| Number of grooves | — | 1 | 2 |
| Height of projections (μm) | — | None | None |
| Width of projections (μm) | — | None | None |
| Number of samples with liquid leakage | 13 | 4 | 6 |
| Evaluation | *2 | *2 | *2 |

*1: Acceptable
*2: Unacceptable

[Test Results]

The gaskets of Examples 1 to 8 were each excellent with a smaller number of samples suffering from the liquid leakage as compared with the gasket of Comparative Example 1 not formed with the groove after the molding. The gaskets of Comparative Examples 2 and 3 each formed with no distinct projection were improved over the gasket of Comparative Example 1, but failed to provide remarkable effects comparable to those of the gaskets of Examples 1 to 8.

projection includes at least one projection extending circumferentially around the circumferential surface portion.

4. The gasket according to claim 1, wherein the film has a thickness of not less than 20 μm and not greater than 50 μm.

5. A prefilled syringe comprising:
   a tubular syringe barrel;
   a plunger combined with the syringe barrel and reciprocally movable in the syringe barrel; and a gasket attached to a distal end of the plunger, the gasket being the gasket according to claim 1.

6. The prefilled syringe according to claim 5, wherein the projection of the gasket contacts the syringe barrel at a contact pressure of not less than 5 MPa.

7. A gasket production method for producing a gasket for use in a prefilled syringe, comprising the steps of:
preparing a gasket forming mold;
molding a gasket in the mold, the gasket having a surface laminated with a film and including a circumferential surface portion;
demolding the gasket from the mold, and then simultaneously forming a groove and a projection each extending circumferentially of the gasket in a portion of the film present in the circumferential surface portion of the gasket.

8. The gasket production method according to claim 7, wherein a laser processing process is employed in the simultaneous groove/projection forming step.

9. The gasket production method according to claim 7, wherein two or more grooves and two or more projections are formed in the simultaneous groove/projection forming step.

\* \* \* \* \*